United States Patent
Vandenberghe et al.

(10) Patent No.: US 12,037,707 B2
(45) Date of Patent: Jul. 16, 2024

(54) METHODS OF MAKING AND USING COMBINATORIAL BARCODED NUCLEIC ACID LIBRARIES HAVING DEFINED VARIATION

(71) Applicants: Massachusetts Eye and Ear Infirmary, Boston, MA (US); The Schepens Eye Research Institute, Inc., Boston, MA (US)

(72) Inventors: Luk H. Vandenberghe, Weston, MA (US); Eric Zinn, Lynn, MA (US); Heikki Turunen, Cambridge, MA (US)

(73) Assignees: Massachusetts Eye and Ear Infirmary, Boston, MA (US); The Schepens Eye Research Institute, Inc., Boston, MA (US)

( * ) Notice: Subject to any disclaimer, the term of this patent is extended or adjusted under 35 U.S.C. 154(b) by 714 days.

(21) Appl. No.: 17/045,120

(22) PCT Filed: Apr. 5, 2019

(86) PCT No.: PCT/US2019/026025
§ 371 (c)(1),
(2) Date: Oct. 2, 2020

(87) PCT Pub. No.: WO2019/195701
PCT Pub. Date: Oct. 10, 2019

(65) Prior Publication Data
US 2021/0156048 A1    May 27, 2021

Related U.S. Application Data

(60) Provisional application No. 62/653,407, filed on Apr. 5, 2018.

(51) Int. Cl.
C40B 50/06    (2006.01)
C12N 15/10    (2006.01)
(Continued)

(52) U.S. Cl.
CPC .......... C40B 50/06 (2013.01); C12N 15/1093 (2013.01); C12Q 1/6897 (2013.01); C40B 40/08 (2013.01)

(58) Field of Classification Search
None
See application file for complete search history.

(56) References Cited

U.S. PATENT DOCUMENTS 4,745,051 A    5/1988    Smith et al.
5,037,384 A    8/1991    Chang
(Continued)

FOREIGN PATENT DOCUMENTS

WO    WO 96/17947    6/1996
WO    WO 2000/24916    5/2000
(Continued)

OTHER PUBLICATIONS

Adachi et al., "MOLPHY: Programs for Molecular Phylogenetics based on Maximum Likelihood," Tokyo Institute of Statistical Mathematics, 1996, ed.
(Continued)

Primary Examiner — Christian C Boesen
(74) Attorney, Agent, or Firm — Fish & Richardson P.C.

(57) ABSTRACT

This disclosure describes compositions, methods, and systems for constructing defined variation in a contiguous functional genetic unit in association with a unique sequence identifier ("a barcode") in a combinatorial manner.

19 Claims, 7 Drawing Sheets

(51) Int. Cl.
  *C12Q 1/6897* (2018.01)
  *C40B 40/08* (2006.01)

(56) References Cited

U.S. PATENT DOCUMENTS

| | | |
|---|---|---|
| 5,387,484 A | 2/1995 | Doany et al. |
| 5,688,676 A | 11/1997 | Zhou et al. |
| 5,691,176 A | 11/1997 | Lebkowski et al. |
| 5,741,683 A | 4/1998 | Zhou et al. |
| 5,817,075 A | 10/1998 | Giungo |
| 6,156,303 A | 12/2000 | Russell et al. |
| 7,906,111 B2 | 3/2011 | Wilson et al. |
| 9,695,220 B2 | 7/2017 | Vandenberghe et al. |
| 9,719,070 B2 | 8/2017 | Vandenberghe et al. |
| 9,782,232 B1 | 10/2017 | Papac |
| 2001/0014788 A1 | 8/2001 | Morris |
| 2002/0081721 A1 | 6/2002 | Allen et al. |
| 2003/0148506 A1 | 8/2003 | Kotin et al. |
| 2004/0216750 A1 | 11/2004 | Snyder et al. |
| 2007/0028928 A1 | 2/2007 | Peyman |
| 2007/0225727 A1 | 9/2007 | Matsuhisa et al. |
| 2008/0090914 A1 | 4/2008 | Enaida et al. |
| 2009/0226531 A1 | 9/2009 | Lyons et al. |
| 2011/0098536 A1 | 4/2011 | Corcosteugi et al. |
| 2012/0093772 A1 | 4/2012 | Horsager et al. |
| 2014/0127801 A1 | 5/2014 | Bakker et al. |
| 2014/0248231 A1 | 9/2014 | Askari et al. |
| 2014/0323354 A1 | 10/2014 | Paul et al. |
| 2015/0182756 A1 | 7/2015 | Peyman |
| 2015/0283265 A1 | 10/2015 | Peyman |
| 2015/0374543 A1 | 12/2015 | Shapiro et al. |
| 2016/0208344 A1 | 7/2016 | Kokoris et al. |
| 2016/0253584 A1 | 9/2016 | Fodor et al. |
| 2016/0296221 A1 | 10/2016 | Morris |
| 2017/0226160 A1 | 8/2017 | Sonntag et al. |
| 2017/0369870 A1 | 12/2017 | Gill et al. |
| 2019/0254870 A1 | 8/2019 | Hopkins |

FOREIGN PATENT DOCUMENTS

| | | |
|---|---|---|
| WO | WO 2000/47757 | 8/2000 |
| WO | WO 03/074714 | 9/2003 |
| WO | WO 2005/033321 | 4/2005 |
| WO | WO 2006/110689 | 10/2006 |
| WO | WO 2007/046703 | 4/2007 |
| WO | WO 2012/162267 | 11/2012 |
| WO | WO 2014/005042 | 1/2014 |
| WO | WO 2014/144495 | 9/2014 |
| WO | WO 2014/160092 | 10/2014 |
| WO | WO 2015/054653 | 4/2015 |
| WO | WO 2016/025878 | 2/2016 |
| WO | WO 2016/094783 | 6/2016 |
| WO | WO 2016/160908 | 10/2016 |
| WO | WO 2017/019994 | 2/2017 |

OTHER PUBLICATIONS

Altschul et al., "Gapped BLAST and PSI-BLAST: A new generation of protein database search programs," Nucleic Acids Res., 1997, 25:3389 3402.
Anisimova et al., "Approximate likelihood-ratio test for branches: A fast, accurate, and powerful alternative," Systematic Biology, 2006, 55:539-52.
Aslanidi et al., "An inducible system for highly efficient production of recombinant adeno-associated virus (rAAV) vectors in insect Sf9 cells," Proc. Natl. Acad. Sci., Mar. 2009, 106(13):5059-5064.
AU Office Action in Australian Appln. No. 2016256894, dated Dec. 13, 2019, 3 pages.
Ausar et al., "Conformational stability and disassembly of Norwalk virus-like particles. Effect of pH and temperature," J. Biol. Chem., 2006, 281:19478-88.
Balazs et al., "Antibody-based protection against HIV infection by vectored immunoprophylaxis," Nature, 2012, 481:81-4.
Balazs et al., "Broad protection against influenza infection by vectored immunoprphylaxis in mice," Nat. Biotechnol., 2013, 31:647-52.
Boutin et al., 2010, "Prevalence of serum IgG and neutralizing factors against AAV types 1, 2, 5, 6, 8 and 9 in the healthy population: implications for gene therapy using AAV vectors," Hum. Gene Ther., 21:704-12.
Brown et al., "A plaque assay for nuclear polyhedrosis viruses using a solid overlay," J. Gen. Virol, Aug. 1977, 36(2):361-364.
Calcedo et al. "Worldwide Epidemiology of Neutralizing Antibodies to Adeno-Associated Viruses," J. Infect. Dis., 2009, 199:381-90.
Cao et al., "Phylogenetic relationships among eutherian orders estimated from inferred sequences of mitochondrial proteins: instability of a tree based on a single gene," J. Mol. Evol., 1994, 39:519-27.
Chen, "Intron splicing-mediated expression of AAV Rep and Cap genes and production of AAV vectors in insect cells," Molecular Therapy, May 2008, 16(5):924-930.
Cheng et al., "Enhanced killing of antibiotic-resistant bacteria enabled by massively parallel combinatorial genetics," Proc Natl Acad Sci USA, 2014, 111(34):12462-12467.
Cole et al., "Human monoclonal antibodies," Mol. Cell. Biol., Sep. 1984, 62(2):109-120.
Darriba et al., "ProTest3: Fast selection of best-fit models of protein evolution," Bioinformatics, 2011, 27(8):1164-5.
Dayhoff et al., "22 a model of evolutionary change in proteins." Atlas of protein sequence and structure. vol. 5. National Biomedical Research Foundation Silver Spring, 1978. 345-352.
Deal et al., "Vectored antibody gene delivery protects against plasmodium falciparum sporozoite challenge in mice," PNAS USA, 2014, 111:12528-32.
Edgar, "MUSCLE: A multipole sequence alignment method with reduced time and space complexity," BMC Bioinform., 2004, 5:113.
EP Extended European Search Report in European Appln. No. 16790158.6, dated Jan. 3, 2019, 5 pages.
EP Extended European Search Report in European Appln. No. 16831443.3, dated Nov. 26, 2018, 20 pages.
EP Extended European Search Report in European Appln. No. 18861359, dated Aug. 13, 2020, 14 pages.
EP Extended European Search Report in European Appln. No. 19782318.0, dated May 28, 2021, 12 pages.
Eyewiki.aao.org [online], "Pars Plana Vitrectomy," Nov. 20, 2019, retrieved on Mar. 27, 2020, retrieved from URL<https://eyewiki.aao.org/Pars_Plana_Vitrectomy>, 7 pages.
Felsenstein, "Maximum Likelihood and Minimum-Steps Methods for Estimating Evolutionary Trees from Data on Discrete Characters," Systematic Biology, 1973, 22:240-9.
Fisher et al., "Recombinant adeno-associated virus for muscle directed gene therapy," 1997, Nature Med., 3:306-12.
Gao et al., "Adeno-associated viruses undergo substantial evolution in primates during natural infections, " PNAS, 2003, 100:6081-6.
Gao et al., "Clades of Adeno-associated viruses are widely disseminated in human tissues," J. Virol., 2004, 78:6381-88.
Gao et al., "New recombinant serotypes of AAV vectors," Current Gene Ther., 2005, 5:285-97.
Gascuel, "BioNJ: An improved version of the NJ algorithm based on a simple model of sequence data," Mol. Biol. Evol., 1997, 14:685-95.
GenBank Accession No. AAC03780.1, "major coat protein VP1 [Adeno-associated virus—2]," Feb. 24, 1998, 1 page.
GenBank Accession No. AAD13756.1, "capsid protein [Adeno-associated virus—5]," Feb. 10, 1999, 1 page.
GenBank Accession No. AAD27757.1, "capsid protein [Adeno-associated virus—1]," Apr. 27, 1999, 1 page.
GenBank Accession No. AAN03857.1, "capsid protein [Adeno-associated virus—8]," Sep. 2, 2002, 1 page.
GenBank Accession No. AAO88201.1, "capsid protein [Non-human primate Adeno-associated virus]," Apr. 9, 2003, 1 page.
GenBank Accession No. AAS99264.1, "capsid protein VP1 [Adeno-associated virus 9]," May 25, 2004, 1 page.
GenBank Accession No. EU368910.1, "Adeno-associated virus isolate AAV6.2 capsid protein VP1 gene, partial cds," Jul. 31, 2008, 1 page.

(56) References Cited

OTHER PUBLICATIONS

GenBank Accession No. EU368926, "Adeno-associated virus isolate rh32.33 capsid protein VP1 gene, partial cds, " Jul. 31, 2008, 1 page.

Gross et al., "Relevance of Assembly-Activating Protein for Adeno-associated Virus Vector Production and Capsid Protein Stability in Mammalian and Insect Cells," Journal of Virology, Aug. 2017, 91(20):e01198-17, 30 pages.

Guindon et al., "New algorithms and methods to estimate maximum-likelihood phylogenies: assessing the performance of PhyML 3.0," System. Biol., 2010, 59:307-21.

Guindon et al., "A simple, fast, and accurate algorithm to estimate large phylogenies by maximum likelihood," Systematic Biology, 2003, 52:696-704.

Henikoff at al., "Amino acid substitution matrices from protein blocks," PNAS, 1992, 89:10915-9.

IN Office Action in Indian Appln. No. 201837006823, dated Mar. 31, 2021, 6 pages.

Janakiraman et al., "A rapid method for estimation of baculovirus titer based on viable cell size," Mar. 2006, J. Virol. Methods, 132(1-2):48-58.

Jones et al., "The rapid generation of mutation data matrices from protein sequences," 1992, Comp. Appl. Biosci., 8:275-82.

JP Office Action in Japanese Application No. 2018-504699 dated Jun. 9, 2020, 6 pages (with English translation).

JP Office Action in Japanese Appln. No. 2018-504699, dated Feb. 16, 2021, 5 pages (with English translation).

Katoh et al., "MAFFT version 5: Improvement in accuracy of multiple sequence alignment," Nuc. Acids Res., 2005, 33:511-8.

Knebel et al. "The promoter of the late p10 gene in the insect nuclear polyhedrosis virus Autographa californica: activation by viral gene products and sensitivity to DNA methylation," Embo. J., May 1985, 4(5):1301-1306.

Kohler et al., "Continuous cultures of fused cells secreting antibody of predefined specificity," Aug. 1975, Nature, 256(5517):495-497.

Kozbor et al., "Specific immunoglobulin production and enhanced tumorigenicity following ascites growth of human hybridomas," J. Immunol. Methods, Jul. 1985, 81(1):31-42.

Lassmann et al., "Kalign, Kalignvu and Mumsa: Web servers for multiple sequence alignment," Nuc. Acids Res., 2006, 34:W596-99.

Lieben, "Genetic screens: CombiGEM—high-throughput identification of combinatorial gene effects," Nat Rev Genet., 2015, 16(10):564-565.

Limberis et al., "Intranasal antibody gene transfer in mice and ferrets elicits broad protection against pandemic influenza," Sci. Transl. Med., 2013, 5:187ra72.

Lock et al., "Rapid, simple, and versatile manufacturing of recombinant adeno-associated viral vectors at scale," Hum. Gene Ther., 2010, 21:1259-71.

Loytynoja et al., "An Algorithm for progressive multiple alignment of sequences with insertions," PNAS USA, 2005, 102:10557-62.

Loytynoja et al., "Phylogeny-Aware Gap Placement Prevents Errors in Sequence Alignment and Evolutionary Analysis," Science, 2008, 320:1632-5.

Manning et al., "Transient immunosuppression allows transgene expression following readministration of adeno-associated viral vectors," 1998, Human Gene Ther., 9:477-85.

Mao et al., "Persistent Suppression of Ocular Neovascularization with intravitreal administration of AAVrh. 10 coding for Bevacizumab," Hum. Gene Ther., 2011, 22:1525-35.

Marten, "AAV vector production: state of the art developments and remaining challenges," Cell Gene Ther. Insights., Dec. 2016, 2(5), 521-551.

Mietzsch et al., "OneBac 2.0: Sf9 Cell Lines for Production of AAV5 Vectors with Enhanced Infectivity and Minimal Encapsidation of Foreign DNA," Human Gene Ther., Jul. 2015, 26(10):688-697.

Mietzsch et al., "OneBac: platform for scalable and high-titer production of adeno-associated virus serotype 1-12 vectors for gene therapy," Human Gene Therapy, Mar. 2014, 25(3):212-222.

Nakai et al., "A limited number of transducible hepatocytes restricts a wide-range linear vector dose response in recombinant adeno-associated virus-mediated liver transduction," J. Virol., 2002, 76:11343-9.

Nakai et al., "Unrestricted hepatocyte transduction with adeno-associated virus serotype 8 vectors in mice," J. Virol., 2005, 79:214-24.

Ncbi.nlm.nih.gov [online], "Facts and Figures Concerning the Human Retina," Jul. 5, 2007, retrieved on Mar. 28, 2020, retrieved from URL<https://www.ncbi.nlm.nih.gov/books/NBK11556/>, 6 pages.

Notredame et al., "T-Coffee: A novel method for fast and accurate multiple sequence alignment," J. Mol. Biol., 2000, 302:205-17.

Paul et al., "Determination of hepatitis E virus seroprevalence by using recombinant fusion proteins and synthetic peptides," 1994, J. Infect. Dis., 169:801-6.

PCT International Preliminary Report on Patentability in International Appln. No. PCT/US2016/031218, mailed on Nov. 16, 2017, 7 pages.

PCT International Preliminary Report on Patentability in International Appln. No. PCT/US2016/044819, mailed on Feb. 8, 2018, 5 pages.

PCT International Preliminary Report on Patentability in International Appln. No. PCT/US2018/53546, dated Mar. 31, 2020, 7 pages.

PCT International Preliminary Report on Patentability in International Appln. No. PCT/US2019/026025, dated Oct. 15, 2020, 7 pages.

PCT International Search Report and Written Opinion in International Appln. No. PCT/US2016/031218, mailed on Aug. 8, 2016, 12 pages.

PCT International Search Report and Written Opinion in International Appln. No. PCT/US2016/044819, mailed on Oct. 31, 2016, 5 pages.

PCT International Search Report and Written Opinion in International Appln. No. PCT/US2018/053546, dated Mar. 22, 2019, 14 pages.

PCT International Search Report and Written Opinion in International Appln. No. PCT/US2019/026025, dated Jun. 12, 2019, 9 pages.

Pettersen et al., "UCSF Chimera—a visualization system for exploratory research and analysis," 2004, J. Comp. Chem., 25:1605-12.

Reeves, "Heterogeneity in the substitution process of amino acid sites of proteins coded for by mitochondrial DNA," 1992, J. Mol. Evol., 35:17-31.

Robert et al., "Manufacturing of recombinant adeno-associated viruses using mammalian expression platforms, " Biotechnol. J., 2017, 12(3):1600193, 16 pages.

Sakhria et al., "Co-Circulation of Toscana Virus and Punique Virus in Northern Tunisia: A microneutralisation-based seroprevalence study," PLOS Negl. Trop. Dis., 2013, 7:e2429.

Samulski et al., "A recombinant plasmid from which an infectious adeno-associated virus genome can be excised in vitro and its use to study viral replication," J. Virol., Oct. 1987, 61(10):3096-3101.

Santiago-Ortiz et al., "AAV ancestral reconstruction library enables selection of broadly infectious viral variants, " gene Therapy, Jul. 2015, 22: 934-946.

Sauerbrei et al. "Seroprevalence of herpes simplex virus type 1 and type 2 in Thuringia, Germany, 1999 to 2006," Euro Survell., 2011, 16(44):3).

Schneider et al., "Empirical codon substitution matrix," BMC Bioinform., 2005, 6:134.

Schon et al., "Retinal gene delivery by adeno-associated virus (AAV) vectors: Strategies and applications," European Journal of Pharmaceutics and Biopharmaceutics, Jan. 2015, 95: 343-352.

Schuster et al., "Biodistribution of adeno-associated virus serotype 9 (AAV9) vector after intrathecal and intravenous delivery in mouse," Frontiers in Neuroanatomy, Jun. 2014, 8: 42 (14 pages).

Schwarz, "Estimating the Dimension of a Model," Ann. Statist. 1978, 6:461-4.

Smith et al., "A simplified baculovirus-AAV expression vector system coupled with one-step affinity purification yields high-titer rAAV stocks from insect cells," Molecular Therapy, Nov. 2009, 17(11):1888-1896.

(56) References Cited

OTHER PUBLICATIONS

Thompson et al., "CLUSTAL W: improving the sensitivity of progressive multiple sequence alignment through sequence weighting, position-specific gap penalties and weight matrix choice," Nuc. Acids Res., 1994, 22:4673-90.

Tseng et al., "Generation and characterization of anti-Adeno-associated virus serotype 8 (AAV8) and anti-AAV9 monoclonal antibodies," J. Virol. Methods, Oct. 2016, 236:105-110.

Urabe et al., "Insect cells as a factory to produce adeno-associated virus type 2 vectors," Hum. Gene Ther., Nov. 2002, 13(16):1935-1943.

Urabe et al., "Scalable generation of high-titer recombinant adeno-associated virus type 5 in insect cells," J Virology, 2006, 80(4):1874-1885.

Wang et al., "Systematic Evaluation of AAV Vectors for Liver directed Gene Transfer in Murine Models, " Mol. Ther., 2010, 18:118-25.

Watanabe et al., "AAVrh10-mediated genetic delivery of bevacizumab to the pleura to provide local anti-VEGF to suppress growth of metastatic lung tumors," Gene Ther., 2010, 17:1042-51.

Weinmann et al., "Next-generation AAV vectors for clinical use: an ever-accelerating race," Virus Genes, Oct. 2017, 53(5):707-713.

Whelan et al., "A general empirical model of protein evolution derived from multiple protein families using a maximum-likelihood approach," Mol. Biol. Evol., 2001, 18:691-9.

Wong et al., "Deciphering Combinatorial Genetics," Annu Rev Genet., 2016, 50:515-538.

Wong et al., "Massively parallel high-order combinatorial genetics in human cells," Nat Biotechnol., 2015, 33(9):952-961.

Wong et al., "Multiplexed barcoded CRISPR-Cas9 screening enabled by CombiGEM," Proc Natl Acad Sci USA, 2016, 113(9):2544-2549.

Xie et al., "AAV-mediated persistent bevacizumab therapy suppresses tumor growth of ovarian cancer," Gynecol. Oncol, 2014, 135: 325-32.

Xu et al., "Seroprevalence of herpes simplex virus types 1 and 2 in pregnant women in the United States," Am. J. Obstet. Gynecol., 2007, 196:43.e1-6.

Yang, "PAML 4: phylogenetic analysis by maximum likelihood, " Mol. Biol. Evol., 2007, 24:1586-91.

Yang, "Maximum-likelihood estimation of phylogeny from DNA sequences when substitution rates differ over sites," Mol. Biol. Evol., 1993, 10:1396-1401.

Yang, "PAML: A program package for phylogenetic analysis by maximum likelihood," Comp. Applic. BioSci., 1997, 13:555-6.

Zinn and Vandenberghe, "Adeno-associated virus: fit to serve," Current Opinion in virology, Oct. 2014, 8: 90-97.

Zinn et al., "In Silico Reconstruction of the Viral Evolutionary Lineage Yields a Potent Gene Therapy Vector," Cell Rep., Aug. 2015, 12(6):1056-1068.

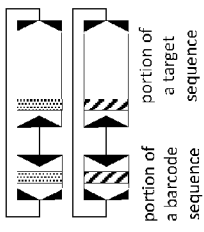
FIG. 3A
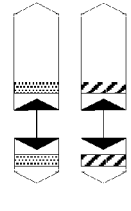
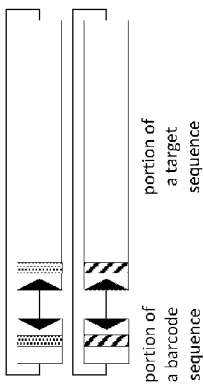
FIG. 3B
FIG. 3C
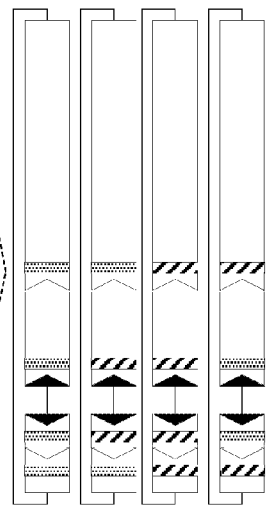
FIG. 3D
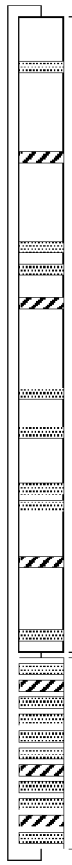

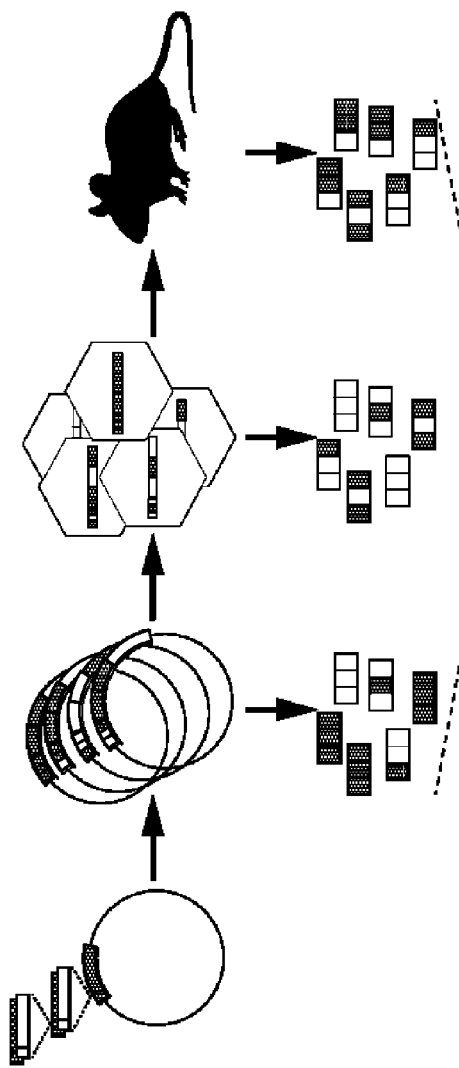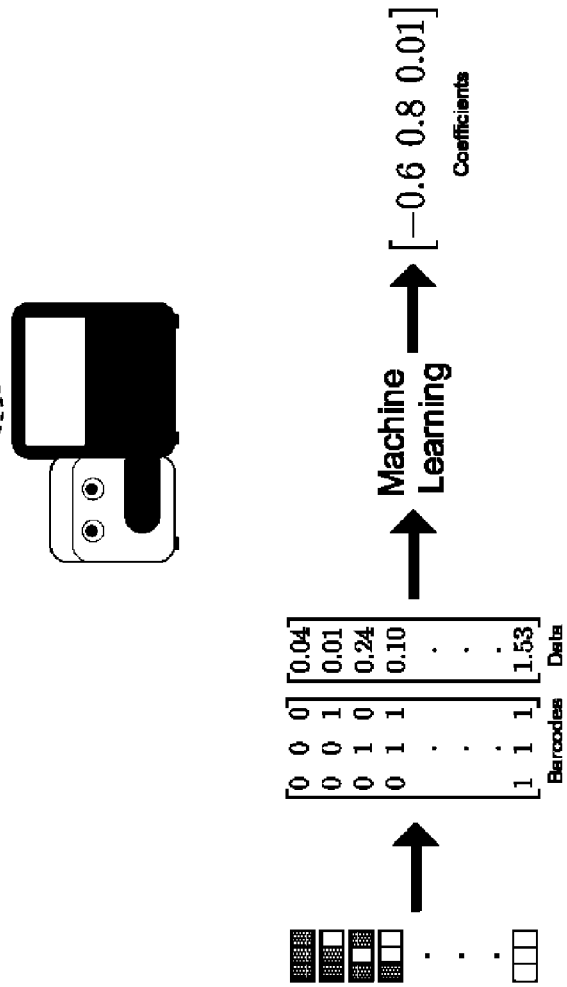
FIG. 4A
FIG. 4B
FIG. 4C
FIG. 4D

METHODS OF MAKING AND USING COMBINATORIAL BARCODED NUCLEIC ACID LIBRARIES HAVING DEFINED VARIATION

CROSS-REFERENCE TO RELATED APPLICATION

This application is a 371 U.S. National Stage entry of PCT/US2019/026025 filed on Apr. 5, 2019, which claims the benefit of U.S. Provisional Patent Application Ser. No. 62/653,407, filed on Apr. 5, 2018. The content of the provisional application is hereby incorporated by reference in its entirety.

TECHNICAL FIELD

This disclosure generally relates to nucleic acid constructs.

BACKGROUND

Combinatorial chemistry and libraries generated using combinatorial chemistry have enhanced the study of complex systems, but some of the current methods still have certain limitations or inefficiencies under certain circumstances. The compositions and methods described herein overcome these limitations and inefficiencies, and are useful under a number of different scenarios. For example, construction of large combinatorial libraries using current methods can be cost prohibitive and time consuming, and many current methods limit or restrict certain features of the library construction (e.g., size, amount and/or degree of variability).

SUMMARY

The methods, compositions, and systems described herein allow for nucleic acids to be generated that contain defined variation in a contiguous functional genetic unit (e.g., open reading frame (ORF), promoter, RNA species, non-coding region, etc.) in a combinatorial manner in association with a unique barcode identifier. The methods, compositions, and systems described herein can be used to evaluate the individual effect of a large numbers of permutations in a combinatorial (i.e., not merely additive) manner.

In general, the disclosure provides methods of generating a combinatorial library, the method including providing a first acceptor sequence having, including, or consisting of a first portion of an acceptor target sequence and a first portion of a corresponding acceptor barcode sequence; providing a first donor sequence having, including, or consisting of a first portion of a donor target sequence and a first portion of a corresponding donor barcode sequence; cleaving the first acceptor sequence between the first portion of the acceptor target sequence and the first portion of the corresponding acceptor barcode sequence; and ligating the first donor sequence into the cleaved first acceptor sequence, thereby producing a second acceptor sequence comprising a second portion of an acceptor target sequence and a second portion of a corresponding acceptor barcode sequence.

These methods can further include providing a second donor sequence including a second portion of a donor target sequence and a second portion of a corresponding donor barcode sequence; cleaving the second acceptor sequence between the second portion of the acceptor target sequence and the second portion of the corresponding acceptor barcode sequence; and ligating the second donor sequence into the cleaved second acceptor sequence, thereby producing a third acceptor sequence comprising a third portion of an acceptor target sequence and a third portion of a corresponding acceptor barcode sequence.

The methods can further include repeating the providing, cleaving, and ligating steps a plurality of times with a third donor sequence and a fourth donor sequence to produce a third acceptor sequence and a fourth acceptor sequence, respectively, until the portions of acceptor target sequences generate a complete target sequence and the portions of corresponding acceptor barcode sequences generate a corresponding complete barcode sequence.

In some embodiments, each portion of the acceptor target sequence can have or include at least one sequence variation and wherein each portion of the corresponding barcode sequence is unique to each of the at least one sequence variation. In various embodiments, the complete target sequence can be selected from the group consisting of a coding sequence, a promoter sequence, an untranslated region, and a polyadenylation signal. For example, the untranslated region can be or include an intron, an miRNA, or an RNA stability element.

In various embodiments, the coding sequence can encode a reporter gene, a viral capsid protein, a gene encoding a therapeutic protein, and a sequence that can be engineered (e.g., an antibody or nuclease enzyme (e.g., Cas, zinc-finger)). In some implementations, the complete barcode sequence is between about 80 base pairs and about 100 base pairs in length.

In some embodiments, the cleaving step includes the use of a Type II restriction endonuclease enzyme.

In another aspect, the disclosure provides methods of screening a combinatorial library for a specific phenotype. These methods include introducing the combinatorial library produced by any of the methods described herein into a host cell under conditions in which the complete target sequence is functional; applying a selective condition on the host cells comprising the combinatorial library; and screening the host cells for the specific phenotype.

These methods can further include identifying a member of the combinatorial library in the host cells exhibiting the desired phenotype, and the identifying step can be or include high-throughput next generation sequencing.

In some embodiments of these methods, the host cells are cultured in vitro. In other embodiments, the host cells are in a living animal, e.g., in a specific tissue within the animal.

In any of these methods, the selective condition can be selected from the group consisting of neutralizing antibody resistance, innate and adaptive immunity resistance, tissue tropism, gene transfer efficiency, gene expression efficiency, gene expression stability, serum stability, yield, affinity-column binding, charged resin binding, thermal stability, a range of pH tolerance, and repeat freeze-thaw tolerance.

In another aspect, this disclosure provides combinatorial libraries that include a plurality of acceptor sequences, wherein each acceptor sequence within the plurality of acceptor sequences includes (i) a complete target sequence comprising a set of sequence variations; and (ii) a corresponding complete barcode sequence physically linked to the complete target sequence.

In some embodiments, the combinatorial libraries include a complete target sequence in each of the plurality of acceptor sequences that is a coding sequence including a set of sequence variations. In various embodiments, the complete barcode sequence in each of the plurality of acceptor sequences is a length that is amenable to high-throughput next generation sequencing. For example, the complete barcode sequence in the plurality of acceptor sequences can be between about 80 base pairs and about 100 base pairs in length. In some embodiments, these combinatorial libraries are made by one of the methods described herein.

The methods described herein allow for inclusion of a barcode sequence that is (a) physically linked to a variable gene sequence, (b) in a manner such that each unique barcode sequence identifies one target sequence variant and vice versa (e.g., the barcode sequence is defined by defined variability at defined positions that corresponds in a known way to the corresponding variation within the target sequence).

The methods described herein allow for the ability to introduce variation within a single open reading frame in a scar-less manner (i.e., without leaving a trace of any manipulation to the DNA sequence). Seamless or scar-less cloning can be accomplished using Type IIS restriction enzymes (e.g., BsaI), which allows for donor and acceptor sequences to be digested in the absence of an internally-located recognition site. Seamless or scar-less cloning also can be achieved using other cloning methods such as Golden Gate cloning (New England Biolab, Catalog No. E1601S), homology based recombination methods (e.g., Gibson Assembly Master Mix, New England Biolab, Catalog No. E2611S), and other methods known in the art.

The methods described herein allow for a large number of combinatorial permutations to be easily (e.g., quickly and inexpensively) evaluated. Since the effects of all combinations are not simply additive, the methods described herein allow for all possible permutations to be readily evaluated. In addition, the methods described herein enable the study of permutations at specific sites of variability rather than only combinations, because the order and location of variation matters, which is not necessarily the case for combinations.

Another of the advantages of the methods described herein is the ability to use the barcode sequences described herein as unique identifiers in high throughput methods such as Next Generation Sequencing (NGS) to determine the frequency of occurrence of a specific event in the target sequence in a quantitative manner. To do so, and as described in more detail herein, each barcode sequence must be retained in a 1:1 linkage with each target sequence.

There are numerous advantages to the methods described herein. For example, the methods described herein can significantly reduce the cost and time required for the construction of libraries that include multiple genetic elements in which variation is defined. In addition, the required association of each donor target sequence with each donor barcode sequence in a 1:1 manner, which carries over into the acceptor sequences, also provides the methods described herein with a number of advantages as discussed in more detail herein.

The methods described herein also overcome a number of limitations with previously established methods. For example, the methods described herein allow for defined variability in defined positions without any restrictions regarding the proximity of the variations (proximity here refers to the number of base pairs separating mutants). For example, there are a number of companies that can synthesize large libraries of mutants provided that all of the variability is constrained to a relatively small number of base pairs. The methods described herein allow those same large libraries to be assembled independent and irrespective of whether the base pairs are proximal (e.g., one or two base pairs apart) or distal (e.g., hundreds or thousands of base pairs apart).

The methods described herein also allow for inclusion and relatively homogeneous representation of all permutations encompassing such variability. To use one representative embodiment, e.g., evaluating complex AAV capsid libraries for gene therapy functionalities, the methods described herein are distinct from other approaches such as directed evolution or bio-panning. Specifically, the variation introduced in the methods described herein is defined and specific, compared to unbiased methods of generating diversity in the AAV capsid. By identifying variation based on structure-function datasets, the likelihood of having informative variants and, consequently, having a greater amount of structural diversity to study/screen, is increased. This is in contrast to unbiased efforts, which often generate a large proportion of dysfunctional diversity, which adds to the noise in any high throughput screening study.

In addition, the methods described herein, along with NGS screening, overcome the need for long read sequencing technology to identify specific variant clones with sites of variation spaced, for example, greater than about 300 bp from each other. Furthermore, other methods often restrict the output of a screen to be a select number of variants that were selected for in a screening, but do not provide relative quantitative measures of performance on any of the variants. Here, quantitative performance data can be obtained on all members (i.e., members that provide a signal over background). The availability of quantitative information on more than one functionality allows for the identification of a vector that has an optimal performance across multiple functions, not just the best performing candidates for a single function. For example, upon retinal injection, vectors that have the lowest degree of bio-distribution with the best retinal gene transfer can be identified. The methods described herein allow for bio-distribution data to be balanced with, for example, retinal gene transfer data to allow for the identification of the optimal vector for this application. Using other methods, the selection of only the best performing retinal gene transfer vectors will not allow for optimization of the bio-distribution, absent a clonal evaluation of each of the lead candidates. Lastly, the methods described herein allow for refined structure-function studies of the AAV capsid, as opposed to the mere identification of variants with increased performance for a particular selective assay.

As used herein, a "target sequence" refers to a sequence within which sequence variation is found. Representative target sequences include, without limitation, coding sequences (e.g., a reporter gene, a viral capsid protein, a gene encoding a therapeutic protein, a sequence that can be or was engineered (e.g., antibodies or nuclease enzymes (e.g., Cas, zinc-finger))), promoter sequences, untranslated regions (e.g., introns, miRNAs, RNA stability elements), and polyadenylation signals. As described herein, a target sequence is compiled from a plurality of "portions of a target sequence." Depending upon the number of variations, the extent of variations, and the positions of variations, a target sequence may be comprised of, for example, two portions up to ten or twenty portions that, when compiled, make up a target sequence, sometimes referred to as a "complete target sequence."

A "portion of a target sequence" may or may not contain one or more variations. For example, in some instances, a portion of a target sequence can include a site of variation, but may contain, for example, a wild type sequence at that site. In other instances, a portion of a target sequence can include a polymorphic site, such that each polymorphism at that site is represented in a different version of that portion of the target sequence.

As used herein, a "barcode sequence" refers to a short sequence (e.g., 4 or 5 nucleotides up to about 300 nucleotides) that can be used to identify the particular sequence variation(s) (or lack thereof) in a corresponding target sequence. As described herein, a barcode sequence is compiled from a plurality of "portions of a barcode sequence," with each portion of a barcode sequence having a sequence that reflects the variation contained within the corresponding portion of a target sequence. The number of portions of barcode sequences that make up a barcode sequence, sometimes referred to as a "complete barcode sequence," correlates directly to the number of portions of target sequences that make up a complete target sequence.

Each "portion of a barcode sequence" indicates a particular variation present in a corresponding portion of the target sequence such that the complete barcode sequence indicates the entirety of the variation contained within the complete target sequence, but in a shorter size than the complete target sequence, and so can be more readily sequenced.

As used herein, "sequence variation" refers to one or more alterations, such as mutations, polymorphisms, insertions, deletions, inversions, duplications, rearrangements, and combinations thereof that can be present in a nucleic acid sequence.

As used herein, a "unique set of sequence variations" refers to a particular combination of sequence variations exhibited along an entire target sequence (e.g., all possible mutations, polymorphisms, insertions, deletions, inversions, duplications, rearrangements, and combinations thereof).

As used herein, "combinatorial library" refers to a compilation of clones that represent many, e.g., all possible, combinations of sequence variation at each position along an entire target sequence.

As used herein, a "corresponding" target and barcode sequence (or portions thereof) refer to the association described herein between sequence variation in a target sequence and a portion of a barcode sequence that allows the precise identification of the sequence variation (i.e., based solely on the sequence of the barcode and without requiring sequencing of the target sequence).

As used herein, "a first acceptor sequence" refers to a first construct having a first portion of an acceptor target sequence and a first portion of an acceptor barcode sequence.

As used herein, "a first donor sequence" refers to a construct having a first portion of a donor target sequence and a first portion of a donor barcode sequence that can be cloned into a first acceptor sequence as described herein.

As used herein, "a second acceptor sequence" refers to the construct that is produced following cloning of a first donor sequence into a first acceptor sequence as described herein. A second acceptor sequence includes a second portion of an acceptor target sequence and a second portion of an acceptor barcode sequence.

As used herein, "a second donor sequence" refers to a construct having a second portion of a donor target sequence and a second portion of a donor barcode sequence that can be cloned into a second acceptor sequence as described herein.

As used herein, a "third acceptor sequence" refers to a construct that is produced following cloning of a second donor sequence into a second acceptor sequence as described herein and includes a third portion of an acceptor target sequence and a third portion of an acceptor barcode sequence, while a "third donor sequence" refers to a construct having a third portion of a donor target sequence and a third portion of a donor barcode sequence that can be cloned into a third acceptor sequence as described herein.

As used herein, a "fourth acceptor sequence" refers to a construct that is produced following cloning of a third donor sequence into a third acceptor sequence as described herein and includes a fourth portion of an acceptor target sequence and a fourth portion of an acceptor barcode sequence, while a "fourth donor sequence" refers to a construct having a fourth portion of a donor target sequence and a fourth portion of a donor barcode sequence that can be cloned into a fourth acceptor sequence as described herein.

Additional acceptor sequences (fifth, sixth, seventh, eight, etc.) and additional donor sequences (fifth, sixth, seventh, eighth, etc.) containing the respective portion (fifth, sixth, seventh, eight, etc.) of a target sequence and respective portion (fifth, sixth, seventh, eight, etc.) of a barcode sequence can be iteratively cloned until a complete target sequence has been constructed as well as a corresponding complete barcode sequence.

As used herein, a "type II restriction endonuclease enzyme" refers to an enzyme that cleaves within or close to its recognition site and does not require ATP hydrolysis for activity. A number of type II restriction enzymes can be used in the methods described herein and include, for example, type IIS (asymmetric recognition site with cleavage occurring at a defined distance), type IIE (two sites required for cleavage, one serving as allosteric effector), type IIF (two sites required for cleavage, both sites are cleaved in a concerted reaction by a homotetrameric enzyme), type IIT (different subunits with restriction and modification activity), type IIG (one polypeptide chain with restriction and modification activity), type IIB (cleavage on both sides of the recognition site), and type IIM (methylated recognition site) enzymes.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIGS. 3A-3D are schematics showing one embodiment of the methods described herein. As in FIG. 1 and FIG. 2, the barcode sequences are shown on the left side of each of the acceptor and donor sequences and the target sequences are shown on the right side of each of the acceptor and donor sequences. FIG. 3A shows that equal ratios of acceptor sequences and equal ratios of donor sequences are mixed; FIG. 3B shows that the acceptor sequences and donor sequences are digested with an enzyme; and FIG. 3C shows that the digested acceptor sequences and donor sequences are then combined and ligated. FIG. 3D shows that complete barcode sequences and complete target sequences can be produced to generate a combinatorial library of variants by repeating the process shown in FIGS. 3A, 3B and 3C.

FIGS. 4A-4D are schematics showing one way in which the methods described herein can be implemented. FIG. 4A shows that, from the methods described herein, a barcoded plasmid library can be created. A barcoded plasmid library can be used to generate a barcoded vector library, and a barcoded vector library can be injected into a mouse or other screening modality, where the barcodes will be present in tissues transduced by the vector; FIG. 4B shows that the barcodes can be isolated at each stage of the method shown in FIG. 4A; FIG. 4C represents a step in which the barcodes are sequenced and the number of times a barcode is present in that sample is quantitated as a "count;" and FIG. 4D shows that the barcodes can be mapped to a phenotype and further can be analyzed using, for example, machine learning.

FIG. 7A shows a scatterplot of barcodes recovered, sequenced, and counted from the livers of two animals infected with a high dose; FIG. 7B shows a scatterplot of barcodes recovered, sequenced, and counted from the livers of two animals infected with a medium dose; and FIG. 7C shows a scatterplot of barcodes recovered, sequenced, and counted from the livers of two animals infected with a low dose.

DETAILED DESCRIPTION

The methods described herein enable the identification of sequence variation that is non-random in location and composition. The methods described herein further enable defined variation to be built into a contiguous functional genetic unit (i.e., a target sequence; e.g., open reading frame (ORF), promoter, RNA species, non-coding region, etc.), which is associated in a combinatorial manner with a short sequence identifier (i.e., a barcode sequence).

In addition, the methods and compositions described herein enable a functional assessment of combinatorial variation within a target sequence (e.g., polymorphisms within a coding sequence, sequence variations within a promoter sequence, etc.) in a high throughput and quantitative manner. The methods and compositions described herein enable the generation of large and complex designer nucleic acid libraries in which a target sequence having defined variation (e.g., a polymorphism within a coding sequence, a sequence variation within a promoter sequence, etc.) within each individual library member is physically linked to a unique barcode identifier sequence.

The methods and compositions described herein allow for variation within a target sequence to be precisely defined in terms of position and composition. Design of the libraries can address desired biological questions (e.g., gene library to introduce combinations of mutations aiming to generate mutant proteins with novel phenotypes), whereas the barcode component allows study of these libraries in a pooled and less complex (and, hence, less expensive) format.

While the complete target sequence can span essentially any length, the complete barcode usually is limited in size (e.g., as few as 4 or 5 nucleotides up to about 300 nucleotides, e.g., 5, 6, 7, 8, 9, 10, 12, 15, 18, 20, 22, 23, 25, 30, 35, 40, 45, 50, 55, 60, 65, 70, 75, 80, 85, 90, 95, 100, 125, 150, 175, 200, 225, 250, 275, or 300 nucleotides), although the length ultimately will depend on the complexity of the library. The methods described herein allow quantitative analysis of the relative abundance of each variant using Next Generation Sequencing (NGS) of only the barcode, which can be sequenced and read extremely quickly. The relatively short size of the barcode allows for an inexpensive, highly accurate sequencing reaction, which, based on the construction of the library, can be directly correlated with the particular sequence variation within each target sequence.

General Methodology

Figure 1:
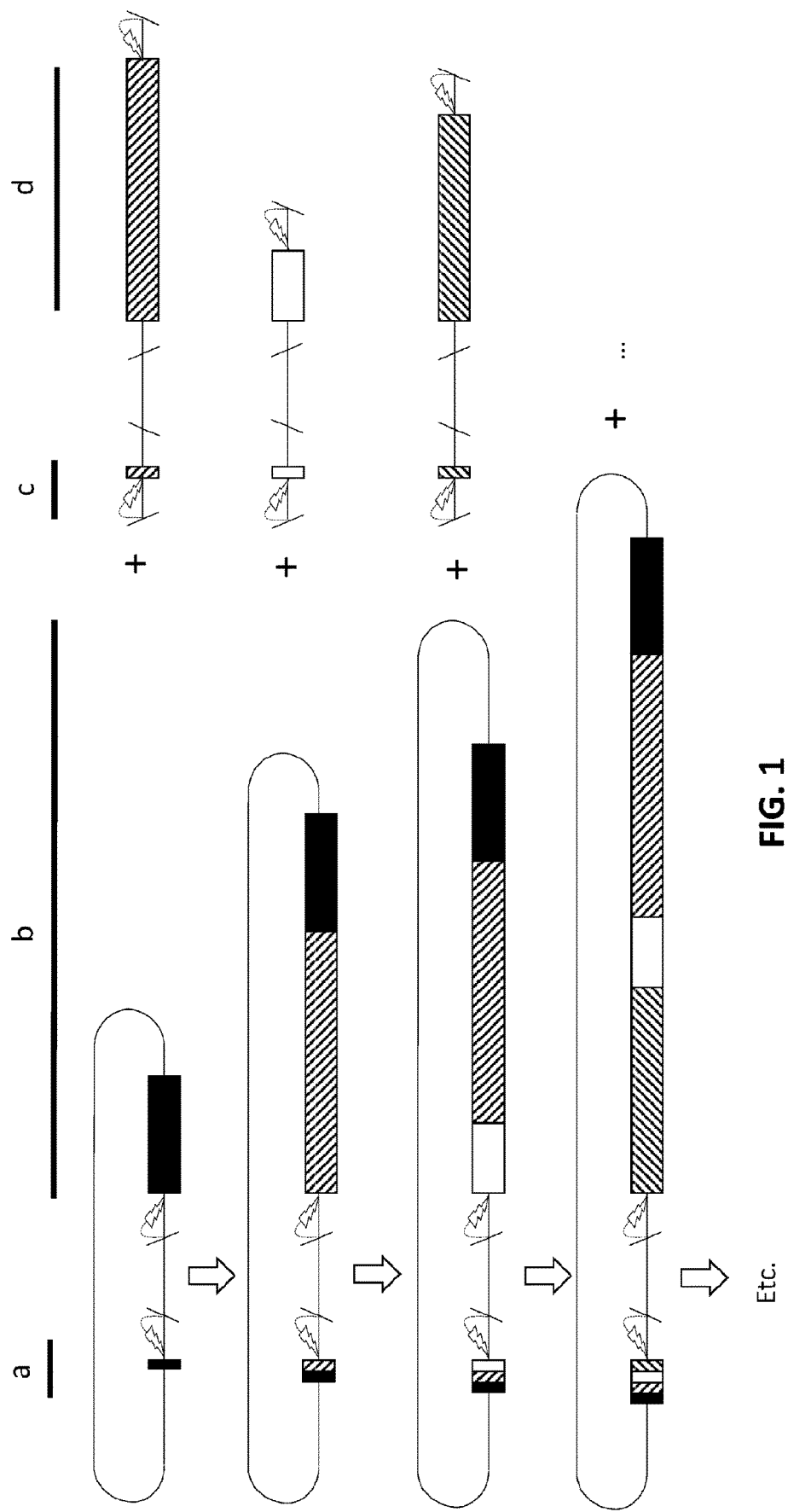
FIG. 1 is a schematic of one embodiment of the methods described herein, but for simplicity, this figure does not show any no sequence variation. The acceptor sequences are shown on the left side of the plus sign, with "a" designating the portions (identified by different patterns) of the acceptor barcode sequences and "b" designating the portions (identified by different patterns) of the acceptor target sequences; and the donor sequences are shown on the right side of the plus sign, with "c" designating the portions (identified by different patterns) of the donor barcode sequences and "d" designating the portions (identified by different patterns) of the donor target sequences. The slash marks between each barcode sequence and each target sequence represent two identical yet inverted Type IIS recognition sites. The hashed lines and thunderbolts attached to the slash marks indicate the location of the cut outside of the recognition site.
Figure 2:
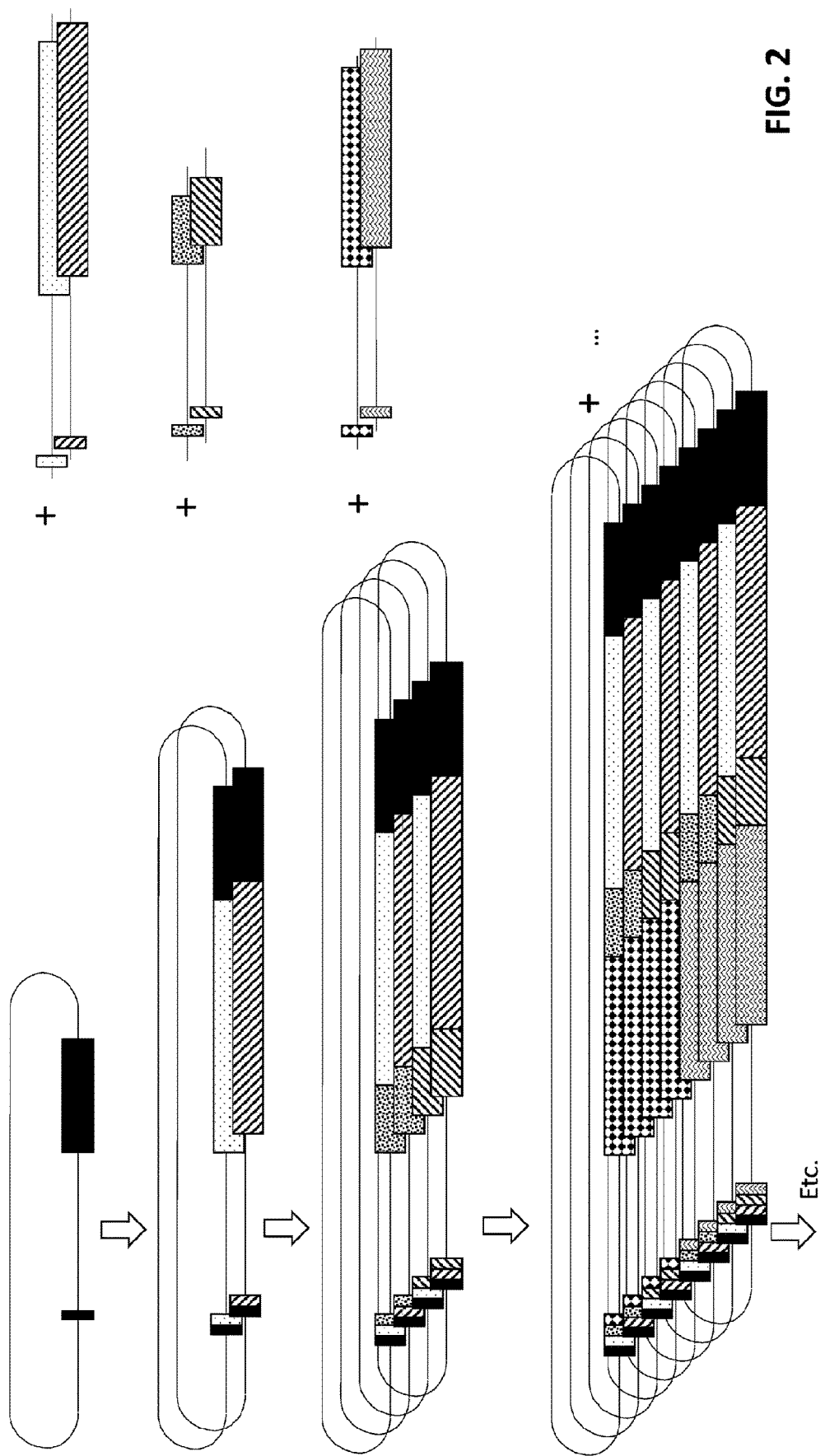
FIG. 2 is a schematic of the embodiment shown in FIG. 1, but with sequence variation present (e.g., shown using patterns; the black portions of the target sequence and the corresponding barcode sequence lack any variation in this embodiment).

FIGS. 1-3 are schematics showing ways in which combinatorial libraries having defined variation (e.g., polymorphisms) within target sequences (e.g., gene sequences) that are uniquely barcoded can be generated. Conceptually, the methods described herein can be used to build a complete target sequence from shorter donor sequences in which variability in individual positions is built from the outside of the construct toward the inside of the construct.

FIG. 1 shows the step-by-step construction of a combinatorial library as described herein. In particular, FIG. 1 shows acceptor sequences (on the left side of the plus sign) and donor sequences (on the right side of the plus sign). For the sake of simplicity in this first figure, none of the sequences include any variation. Each acceptor sequence includes a target sequence portion and a barcode portion, referred to herein as a portion of an "acceptor target" sequence (the region designated as "b" in FIG. 1) and a portion of a corresponding "acceptor barcode" sequence (the region designated as "a" in FIG. 1). Similarly, each donor sequence includes a target sequence portion and a barcode portion, referred to herein as a portion of a "donor target" sequence (the region designated as "d" in FIG. 1) and a portion of a corresponding "donor barcode" sequence (the region designated as "c" in FIG. 1). Upon cleavage of the acceptor and donor sequences with, e.g., a Type II restriction enzyme (enzyme binding site and offset cleavage site indicated by the slash marks and thunderbolts, respectively), a donor sequence is ligated into the cleaved acceptor sequence to produce a "new" acceptor sequence. As described in more detail herein, the acceptor sequences grow as each donor sequence is incorporated until, eventually, a complete target sequence and a corresponding complete barcode sequence are generated.

Specifically, for example, a first acceptor sequence (black in FIG. 1), including a first portion of an acceptor target sequence (on the right of the slash marks) and a first portion of a corresponding acceptor barcode sequence (on the left of the slash mark), is cleaved and a first donor sequence (left-diagonal pattern in FIG. 1), including a first portion of a donor target sequence and a first portion of a corresponding donor barcode sequence, is ligated into a first cleavage site such that the portions of the target sequences are adjacent to one another and the portions of the barcode sequences are adjacent to one another.

The resulting construct then can be used as an acceptor sequence (black/left-diagonal in FIG. 1; referred to herein as the "second" acceptor sequence) and is cleaved, and a second donor sequence (white sections in FIG. 1), including a second portion of a donor target sequence and a second portion of a corresponding donor barcode sequence, is ligated into a second cleavage site such that the portions of the target sequences are adjacent to one another and the portions of the barcode sequence are adjacent to one another. Due to the physical separation of the recognition sites and cleavage sites for TypeIIS enzymes, the recognition site is removed, and then replaced by the incoming fragment, at east step. The same enzyme, therefore, can be used iteratively in each cloning step.

The resulting construct then can be used as another acceptor sequence (black/left diagonal/white in FIG. 1; referred to herein as the "third" acceptor sequence) and is cleaved, and a third donor sequence (right-diagonal in FIG. 1), including a third portion of a donor target sequence and a third portion of a corresponding donor barcode sequence, is ligated into the cleavage site such that the portions of the target sequences are adjacent to one another and the portions of the barcode sequences are adjacent to one another, resulting in a "fourth" acceptor sequence (black/left-diagonal/white/right-diagonal in FIG. 1).

Once the desired number of donor sequences have been iteratively cloned into acceptor sequences, a complete target sequence and a complete barcode sequence are produced. It is understood that, if the target sequence is going to be screened by functionality, cloning of the portions of target sequences to produce the complete target sequence needs to be in-frame or the portions of the target sequences must be otherwise operably linked to one another. The cloning reactions can be tightly controlled using, for example, iterations with individual donor sequences and subsequent washes to remove un-ligated donor sequences prior to the next iteration.

In addition, the methods described herein also require that the acceptor sequences always (e.g., in each iterative cycle) retain a molecular linkage between the nascent barcode sequence and the nascent target sequence, particularly during insertion of the donor sequence. This can be achieved by using a vector (e.g., a plasmid; represented by the thin black line in FIG. 1) that is only cleaved at the desired insertion site within the acceptor sequence (between the target sequence portion(s) and the barcode portion(s) in FIG. 1) Simply by way of example, ligation of donor sequences into acceptor sequences can be achieved by maintaining the acceptor sequences as circular plasmids and internally digesting the plasmid at the barcode-target sequence junction (e.g., with Type IIS restriction enzyme digestion) to insert the donor sequence into the acceptor sequence such that the donor barcode sequence remains linked to the corresponding donor target sequence via the plasmid backbone.

Following each round of cloning, the resulting acceptor sequence corresponds to a compilation of portions of donor target sequences and portions of donor barcode sequences from the previous rounds of cloning. Significantly, the methods described herein require that the compilation of portions of acceptor barcode sequences mirrors the compilation of portions of acceptor target sequences (as shown in FIG. 1). As described herein, a complete target sequence and a complete barcode sequence eventually are produced.

The target sequence (e.g., the 5' end in FIG. 1) and the barcode sequence (e.g., the 3' end in FIG. 1) (and the portions of each) can be a minimum of about 10-12 bp apart up to virtually any distance, provided that the distance does not significantly disrupt the reliable and efficient cloning of donor sequences into acceptor sequences. In practice, however, it is likely that the distance between the target sequence and the barcode would not be more than about 2 kb, in order to save time and improve resolution.

FIG. 2 is a schematic showing the step-by-step construction of a combinatorial library as described herein with the introduction of variation into the target sequences. The schematic shown in FIG. 2 uses a simple alternative variation (lined vs. stippled) in each instance, which exponentially increases the diversity of the library following repeated or iterative cycles. Therefore, the methods described herein can accommodate an enormous amount of complexity in the combinatorial possibilities. As shown in FIG. 2, the step-wise construction of acceptor sequences (left side) and donor sequences (right side) in which variation is present (e.g., represented in FIG. 2 by left-diagonal vs. light-stipple, right-diagonal vs. dark-stipple, and wavy line vs. diamond pattern) results in the construction of a library of acceptor sequences in which known variations in the complete target sequence are reflected in the complete barcode sequence. There is no variation in the black acceptor sequence in this example, but there could be one or more variations.

Known variability within a complete target sequence, which, as described herein, is directly reflected in the complete barcode sequence, can be generated by breaking up the target sequence into smaller portions such that each portion of a donor target sequence incorporated into the acceptor sequences contains defined variability, which is reflected in the corresponding donor barcode sequence, generally in some sort of simplistic or shorthand manner (e.g., a particular nucleotide at a particular position (e.g., a "G" at the $4^{th}$ position) in the first portion of the donor barcode corresponds to variant "A" in the first portion of the donor target sequence whereas a different nucleotide at the particular position (e.g., a "T" at the $4^{th}$ position) in the first portion of the donor barcode corresponds to variant "B" in the first portion of the donor target sequence). Significant combinatorial diversity of acceptor sequences can be generated using multiple cycles of this strategy. See, for example, FIG. 2.

FIGS. 3A-3D are another schematic showing a set of acceptor sequences (left) and donor sequences (right). The white bars correspond to the donor and acceptor barcode and target sequences; the stippled and diagonal-lined bars indicate a site of variation (e.g., a polymorphism). As in FIG. 1 and FIG. 2, the barcode sequences are shown on the left side of each of the acceptor and donor sequences and the target sequences are shown on the right side of each of the acceptor and donor sequences.

FIG. 3A shows that equal ratios of acceptor sequences and equal ratios of donor sequences are mixed. In FIG. 3A, the first cycle of two different acceptor sequences (stipple or left-diagonal) and two different donor sequences (stipple or left diagonal) leads to four different combinations (stipple/stipple; stipple/left-diagonal; left-diagonal/left-diagonal; left-diagonal/stipple). The acceptor sequences are designed to contain a terminal portion (e.g., a 3' portion) of a target sequence (e.g., a gene of interest) linked to a portion (e.g., a terminal or 5' portion) of a barcode sequence. The acceptor sequences can be provided in more than one version, with each version being distinct from one another in a defined manner (e.g., in the sequence of that particular portion of the target sequence (e.g., a single nucleotide polymorphism, a mutation)), where each version of the portion of the target sequence is associated with a distinct portion of a barcode sequence that is representative of the variation in the target sequence. Although the figures herein show the barcode sequences on the 5' of the target sequences, it is understood that, within a library, the barcode sequences can be either 5' or 3' of the target sequences.

In FIG. 3B, one or more donor sequences are inserted, in a scar-less fashion (e.g., using Type IIS restriction enzyme digest), into the acceptor sequences. As used herein, "scarless" or "seamless" insertion refers to cleavage and recombination or insertion without the introduction of any changes (e.g., introduction of additional nucleotides or loss of one or more nucleotides). The design of these donor sequences is analogous to the design of the acceptor sequences in that they have a portion of a target sequence linked to a portion of a barcode, however the portions of the target sequence and the portions of the barcode in the donor sequences are internal to the corresponding target and barcode sequences in the acceptor sequences. In this iterative process, the newly fused donor and acceptor sequences become the acceptor sequence in a subsequent cycle. The methods described herein allow the target sequences and the barcode sequences within the acceptor sequences to be extended in a stepwise and controlled fashion.

The pool of combinations produced in FIG. 3C can be used as acceptor sequences for a further round of assembly with a different donor sequence (e.g., FIG. 3A). FIG. 3D shows that complete barcode sequences and complete target sequences can be produced to generate a combinatorial library of variants by repeating the process shown in FIG. 3A, FIG. 3B and FIG. 3C. Any or all of these sequences (e.g., the portions of the target sequences and the portions of the barcode sequences) can be provided in multiple versions. For example, in FIGS. 3A-D, two different fragments are shown, all with similarly defined variation. Insertion of donor sequences into acceptor sequences leads to combinatorial diversity based on the different acceptor and donor sequences.

The iterative process can be terminated when the target sequence (e.g., a gene of interest), including all the relevant sequence variants within the target sequence, are fully assembled and complete.

Features Provided by the Methods Described Herein

The methods described herein allow for sequential buildup of acceptor target sequences by the addition of different donor sequences that each contains one or more sites of defined and unique variability.

The methods described herein enable combinatorial analysis, in that more than one donor sequence can be provided at each sequential step to generate all possible permutations of each of the predefined sites of predefined variation.

The methods described herein enable the detection of a small barcode sequence that is directly reflective of the defined variability within the larger target sequence.

The methods described herein also allow for multiplex batch readout (i.e., the ability to distinguish the contribution of individual variation within a member of a given library by its unique barcode).

The methods described herein enables seamless or scarless cloning of donor sequences within acceptor sequences using, e.g., Type II restriction enzymes, with results in the ability to generate contiguous, and, in some cases, functional, genetic elements such as open reading frames, promoter regions, or types of non-coding RNA.

As discussed herein, the required association of each donor target sequence with each donor barcode sequence in a 1:1 manner, which carries over into the acceptor sequences, provides the methods described herein with a number of advantages. For example, the 1:1 ratio of target to barcode sequences allows for a facile readout of a short nucleic acid sequence that provides information on the target sequence variability, e.g., information on the order/sequence/combination of how the variability came together in a single phase read using Next Generation Sequencing technology (e.g., the Illumina MiniSeq®, NextSeq®, HiSeq®, or NovaSeq® platforms or others (e.g., PacBio, 10× Genomics) can be used to provide a very high sequence depth). In addition, because these platforms are able to independently sequence every barcode in the sample one-time, the 1:1 ratio of target to barcode sequences allows for a quantitative measure of function by evaluating the relative abundance of a particular barcode compared to others, and also allows for a method to control for contribution of the difference in relative abundance in input of a selective screening assay to the observed effect size in the output.

The methods described herein, and specifically the association of the target sequence with a barcode sequence in a 1:1 manner, also allows for (semi)-exhaustive readout of library members, which allows for identification of both negatively- and positively-selected members of a given library. Due to the sensitivity of the readout, the relative counts on all the barcode sequences represented in a sample can be determined, which provides information on those members that are positively selected versus those that are negatively selected. In one example of this embodiment, using an AAV example, both efficient and inefficient liver transduction can be used as a screen depending on whether one wants to target or de-target the liver, respectively.

In addition, the 1:1 ratio of target sequence to barcode sequence allows for readouts across multiple functional parameters, which, in turn, allows for parallel multi-parameter optimization. That is, given that the barcode sequence can be determined for more than one selective assay, the optimal library member (i.e., target sequence) across multiple selective functional assays can be determined, and the contribution of each of these parameters/functions can be weighted. For example, in one embodiment of a promoter example, one may want to identify a promoter that is highly active in astrocytes and microglia yet not in neurons, or in one embodiment of an AAV example, one may want to identify a vector that targets liver greatly, kidney moderately, and muscle minimally.

Further, the 1:1 target sequence to barcode sequence ratio allows for direct structure-function readout without the need to identify what genetic element set of variables is associated with a certain barcode sequence. The methods described herein allow for structure-function studies on larger sets of combinatorial variant sets of a given genetic element with quantitative assessment of function directly associated with composition. This allows for powerful determinations of structural domains of functional relevance in a high throughput manner in which the significance is increased by the number of parallel tested permutations and also allows for the ability to generate larger datasets sampling of complex structural and functional biological interactions that may be epistatic (e.g., AAV viral capsid structure, promoter element combinations).

The methods described herein also overcome a number of limitations with previously established methods. For example, the methods described herein allow for defined variability in defined positions without any restrictions regarding the proximity of the variations (proximity here refers to the number of base pairs separating mutants). For example, existing methods can synthesize large libraries of mutants provided that all of the variability is constrained to a relatively small number of base pairs. The methods described herein allow those same large libraries to be assembled independent and irrespective of whether the base pairs are proximal (e.g., one or two base pairs apart) or distal (e.g., hundreds or thousands of base pairs apart).

The methods described herein allow for inclusion and relatively homogeneous representation of all permutations encompassing such variability.

In addition, the methods described herein allow for inclusion of a barcode sequence that is (a) physically linked to a variable gene sequence, (b) in a manner such that each unique barcode sequence identifies one target sequence variant and vice versa (e.g., the barcode sequence is defined by defined variability at defined positions that corresponds in a known way to the corresponding variation within the target sequence).

The methods described herein allow for the ability to introduce variation within a single open reading frame in a scar-less manner (i.e., without leaving a trace of any manipulation to the DNA sequence). Seamless or scar-less cloning can be accomplished using Type IIS restriction enzymes (e.g., BsaI), which allows for donor and acceptor sequences to be digested in the absence of an internally-located recognition site. Seamless or scar-less cloning also can be achieved using other cloning methods such as Golden Gate cloning (e.g., Golden Gate Assembly Kit, NEB, Catalog #E1601S), homology based recombination methods (e.g., Gibson Assembly Master Mix, NEB, Catalog #E2611S), and other methods known in the art.

To use one representative embodiment, e.g., evaluating complex AAV capsid libraries for gene therapy functionalities, the methods described herein are distinct from other approaches such as directed evolution or bio-panning. Specifically, the variation introduced in the methods described herein is defined and specific, compared to unbiased methods of generating diversity in the AAV capsid. By identifying variation based on structure-function datasets, the likelihood of having informative variants and, consequently, having a greater amount of structural diversity to study/screen, is increased. This is in contrast to unbiased efforts, which often generate a large proportion of dysfunctional diversity, which adds to the noise in any high throughput screening study.

In addition, the methods described herein, along with NGS screening, overcome the need for long read sequencing technology to identify specific variant clones with sites of variation spaced, for example, greater than about 300 bp from each other. Furthermore, other methods often restrict the output of a screen to be a select number of variants that were selected for in a screening, but do not provide relative quantitative measures of performance on any of the variants. Here, quantitative performance data can be obtained on all members (i.e., members that provide a signal over background). The availability of quantitative information on more than one functionality allows for the identification of a vector that has an optimal performance across multiple functions, not just the best performing candidates for a single function. For example, upon retinal injection, vectors that have the lowest degree of bio-distribution with the best retinal gene transfer can be identified. The methods described herein allow for bio-distribution data to be balanced with, for example, retinal gene transfer data to allow for the identification of the optimal vector for this application. Using other methods, the selection of only the best performing retinal gene transfer vectors will not allow for optimization of the bio-distribution, absent a clonal evaluation of each of the lead candidates. Lastly, the methods described herein allow for refined structure-function studies of the AAV capsid, as opposed to the mere identification of variants with increased performance for a particular selective assay.

In particular, the methods described herein can be used to evaluate:

a) some or all permutations of codons encoding one of two amino-acids at positions 213 (A or G), 333 (P or L), 577 (A or L) and 933 (N or Q) within a particular open reading frame (ORF) with the goal of evaluating the impact of each residue change on protein function;

b) some or all permutations of the presence (insertion) or absence (deletion) of each domain within a multi-domain protein with the goal of evaluating which combinations of domains may be required and dispensable for protein function; and c) some or all permutations of transcription factor binding domains in a particular position or order within a promoter sequence with the goal of driving expression in a specific manner.

The methods described herein also provide the ability to combine any combination(s) of the above into a potent in vivo gene transfer modality such as AAV or lentivirus to interrogate function in complex biological systems in a cost-effective manner. For example, the multiplex nature of the methods described herein and the subsequently produced combinatorial library can be used to minimize the number of animals enrolled in animal studies (e.g., all members of the combinatorial library can be compared in one or a few animals).

One example of this embodiment is when a library generated as described herein (e.g., an "input library") is injected into a mouse via an IV route to evaluate liver targeting (or, e.g., promoter expression). Hepatocytes are harvested from the mouse and DNA and RNA from the hepatocytes are isolated for analysis. The "output libraries" correspond to the representation of barcode sequences in the DNA and/or RNA. Since barcode sequences are present in the input library along a certain distribution, one needs to control for that distribution to interpret whether there is enrichment (i.e., positive selection) or de-enrichment (i.e., negative selection) of a particular barcode sequence and, hence, the corresponding member of the library. This can be done by sampling the distributions of barcode sequences (i.e., the counts per barcode in the input library and the output library following the screen) and normalizing the output library and the input library on a barcode-by-barcode manner. Simply put, each per barcode count is converted to and expressed as a proportion of the total count for each library for further analysis.

The methods described herein implement the following features: a) the ability to exhaustively capture all intended variations in a DNA library; b) the ability to have a quantitative readout of functional performance on each of the members of a DNA library; and c) the ability to transfer a DNA library into in vitro and/or in vivo (e.g., mammalian) systems.

In Vivo and In Vitro Embodiments

The following embodiments are representative examples of ways in which the methods described herein can be applied. The following embodiments are not intended to be exhaustive or limiting.

In some embodiments, the methods described herein can be used to study the impact of known single nucleotide polymorphisms (SNPs) in a gene of interest, individually or in all combinations.

In other embodiments, the methods described in this document can be used to study the impact of discreet functional variation of a homologous gene sequence between species.

In certain embodiments, such methods can be used to engineer a conformational domain (e.g., binding pocket) of a protein in a combinatorial manner, where the conformational domain is composed of variable domains.

In yet other embodiments, the methods described herein can be used to evaluate synthetic libraries of coding and/or non-coding sequences in which sites of defined variation can be tested in a combinatorial manner.

Thus, in general, the present disclosure includes methods of screening a combinatorial library for a specific phenotype. These methods include introducing a combinatorial library produced by the methods described herein into a host cell under conditions in which the complete target sequence is functional; applying a selective condition on the host cells that include the combinatorial library; and screening the host cells for the specific phenotype. These methods can further include identifying a member of the combinatorial library in the host cells exhibiting the desired phenotype.

For example, in certain implementations, the identifying step can include high-throughput next generation sequencing and the cells can be cultured in vitro or the cells can be within a host animal model and are thus in vivo host cells, e.g., as part of a specific tissue in the animal. In these methods, the selective conditions, e.g., a selective pressure, can be neutralizing antibody resistance, innate and adaptive immunity resistance, tissue tropism, gene transfer efficiency, gene expression efficiency, gene expression stability, serum stability, yield, affinity-column binding, charged resin binding, thermal stability, a range of pH tolerance, and repeat freeze-thaw tolerance.

In further embodiments, the methods described in this document can be used to evaluate libraries that bring together various transcriptional regulators (e.g., transcription factor binding sites, enhancer elements, etc.) in a combinatorial manner to achieve higher or more specific expression from a construct.

In some embodiments, such methods can be used for AAV capsid analysis, screening, and optimization. For example, libraries of capsids derived from adeno-associated virus (AAV) and used for gene transfer and gene therapy can be generated and evaluated using the methods described herein. Briefly, there is an interest in permutating specific residues on the AAV capsid at defined positions across the entirety of the 2.4 kb open reading frame. In one application, this variation is defined by maximum likelihood prediction of the ancestral states of the capsid protein within a lineage of primate AAVs (variation defined in Zinn et al., 2015, Cell Rep., 12(6):1056-68). The challenge then is to (a) generate and (b) exhaustively evaluate the diversity. The methods described herein allow such goals to be met. The libraries generated in this way can be transformed into viral libraries, which, in turn, can be screened in a selective assay for functions such as in vitro or in vivo tropism, affinity to certain ligands, etc.

In other embodiments, the methods described herein can be used for therapeutic cDNA abbreviation, in order for larger cDNA and transgenes to be accommodated within AAV's packaging limitation. For example, libraries of target sequences (e.g., genes) that are too long for delivery in a single AAV vector, which has a transgene capacity of <4.5 kb, can be generated and evaluated using the methods described herein. In this embodiment, the aim is to truncate larger genes to generate functional mini-genes of a size compatible with AAV packaging. Generally, the desire is to use the methods described herein on target sequences that have multiple repetitive domains. The specific approach introduces variation in a particular set of positions across the gene that either incorporates a domain or omits it. These libraries can be screened in an assay that leads to a selective benefit if there is a therapeutic effect.

In certain embodiments, the methods described in this document can be used for promoter optimization. For example, libraries of promoter sequences that include combinations of various elements relevant to transcriptional regulation (e.g. transcription factor binding sites, enhancer sequences, etc.) can be generated and evaluated using the methods described herein. These promoter sequences can be evaluated in library format following gene transfer into an in vitro or in vivo system and promoter functionality can be evaluated based on, for example, the barcode sequence(s) associated with various RNA expression levels.

In still other embodiments, such methods can be used for screening gene products with regenerative potential. For example, combinatorial libraries of target sequences with regenerative potential can be barcoded as described herein and used in CRISPR guide RNAs to allow for lineage tracing of the regenerated cells and identification of the corresponding library sequence that induced the regeneration.

In additional embodiments, the methods described herein can be used for affinity ligand selection and optimization. For example, varied antibody, nanobody, or other ligands can be generated and evaluated using this methodology and then screened using the barcodes.

In accordance with the present invention, there may be employed conventional molecular biology, microbiology, biochemical, and recombinant DNA techniques within the skill of the art. Such techniques are explained fully in the literature.

EXAMPLES

Example 1—Exemplary Time and Cost Comparison of Current Methods vs. the Methods Described Herein There are numerous advantages to the methods described herein. For example, the methods described herein can significantly reduce the cost and time required for the construction of libraries that include a genetic element in which certain variation is defined.

The Anc80 scaffold sequence (see, for example, U.S. Pat. Nos. 9,695,220 and 9,719,070) contains 11 sites at which one of two amino acids can be present. This number of variations corresponds to 2'11=2048 different nucleic acid sequences (i.e., 2048 different variants). If the overall length of the Anc80 scaffold sequence is 2400 bp, and it is assumed that nucleic acid synthesis costs $0.10 per base pair (bp), irrespective of fragment length, then the synthesis and sequencing of such a library would cost about $491,520 ($0.10/bp×2400 bp×2048 different nucleic acids) using current synthesis and sequencing methodologies. In addition, it is unclear what the timeline for such synthesis and sequencing would be, as it is assumed that this number of sequencing reactions would bottleneck any available capacity of commercial vendors if done in parallel and take a long time if done in series if we estimate one week/kb synthesized.

On the other hand, synthesis and identification using the methods described herein requires significantly less time and cost. In a design in which each of the 11 sites of variation is introduced individually, the approximate cost would be about $660 ($0.10/bp×300 bp×11 sites of variance×2 variables per site). If we presume three days to process, transform, pick, and verify each assembly step, the approximate time for assembling such a library is estimated to be about 1 month using current technologies. In a design in which positions of variants are grouped or bundled in larger synthetic blocks (e.g., 4+4+3 positions), the cost would be about $3800 ($0.10/bp×[2^4×1000 bp+2^4×1000 bp+2^3× 750 bp]), and the approximate time for assembling such a library is estimated to be 1 to 2 weeks using current technology.

Example 2—Screening a Library of Ancestral AAV Scaffold Sequences

FIGS. 4A-4D are schematics of the experimental protocol followed for the present example. In some instances, the linked barcode is further compressed into a code that captures both the biology of the variant and makes it an acceptable input for machine learning.

FIG. 4A illustrates the possible sources of barcode sequence available for further analysis. The library is initially assembled as per FIGS. 1 and 2 to create the barcoded double-stranded DNA plasmid library. This plasmid library can be used to direct the production of the AAV vector library upon co-transfection of 293 cells with appropriate helper plasmids. Each vector packages the coding sequence that directed that particular variant's primary structure and its linked barcode. Finally, these vectors can be introduced into a mouse (and localized to one or more tissues, depending on the parameters of the vector) or other in vivo or in vitro screening methodology.

FIG. 4B shows that, at any of the steps listed above (e.g., plasmid, vector, or tissue), the barcodes can be isolated using traditional molecular biological techniques. Barcode counts may change depending on the source. Further processing to amplify and add Illumina indices (unique sequences at the 3' and 5' ends to allow multiplexing of samples) produces a linear double-stranded DNA molecule that now is an appropriate substrate for next-generation sequencing (NGS).

FIG. 4C depicts a cartoon high-throughput next-generation sequencing platform (e.g., Illumina MiSeq®/NovaSeq® methodologies) for sequencing and counting the barcodes.

FIG. 4D shows that the output from the sequencing platform is the nucleotide sequence of the barcode and its abundance in that sample. The sequence can be converted to a numerical code. The numerical code representing the barcode sequence and any other data garnered from the same experiment (e.g., barcode count, tissue type, and mouse strain) can be converted into a numerical signifier, which can serve as input for machine learning. Machine learning may identify patterns and significance that can be expressed as, for example, coefficients of correlation.

Figure 5B:
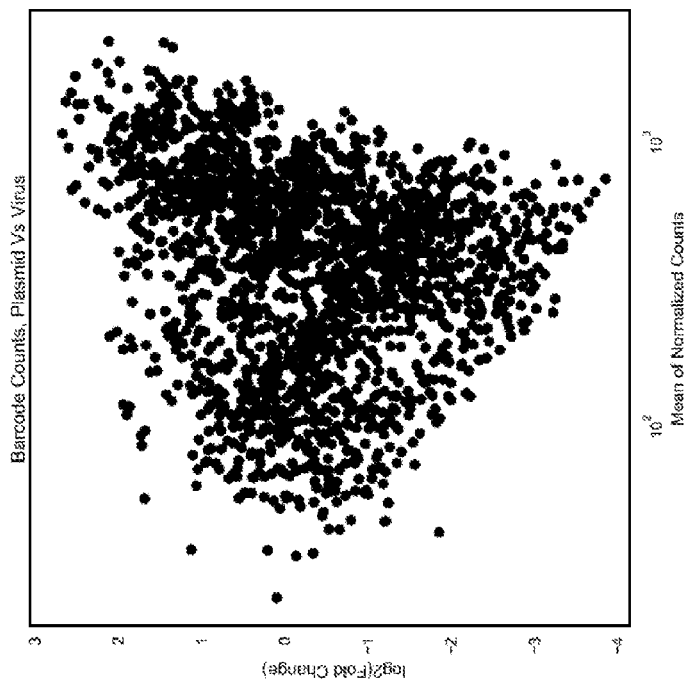
FIG. 5B is a scatterplot that demonstrates a large dynamic range of a phenotype quantified by next generation sequencing. In this instance, a library of AAV capsid mutants reveals differential rates of assembly and genome packaging.
Figure 5A:
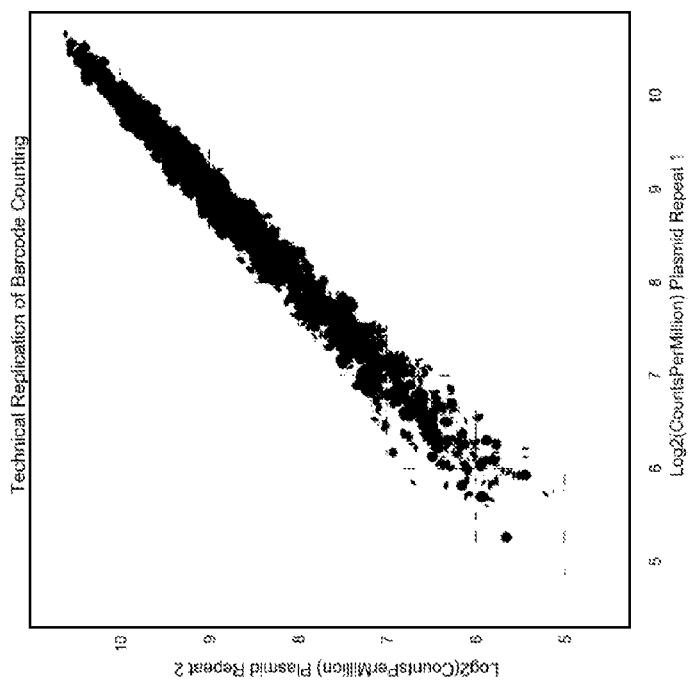
FIG. 5A is a scatterplot that demonstrates the technical reproducibility of the technique, i.e., that barcodes sequenced and counted from the emergent library of mutants is repeatable over different days and in independent preparations.

FIG. 5A is a scatterplot that shows the results from a particular NGS validation and demonstrates the technical reproducibility of the technique, i.e., that barcodes sequenced and counted from the emergent library of mutants is repeatable over different days and in independent preparations. Each point is a specific variant whose X-Y coordinate is defined by their normalized abundance in the compared samples. The aim of the experiment was to test the hypothesis that the platform pipeline described in FIG. 4 was robust, repeatable, and sensitive enough to recover and identify all of the barcodes expected in a plasmid library. The same library was processed twice, independently and on different days, and analyzed. Encouragingly, all barcodes were present in all reads of the plasmid, and the technical replicates were highly correlated (Spearman's R of 0.99). For example, Anc80L65 was present at 57 counts per million (CPM; log 2(57)~5.8) and exhibited an average representation of about 488 CPM, a highest CPM of 1102 and a lowest CPM of 15. This result indicates that the platform faithfully counts the barcodes present in any preparation.

FIG. 5B is a scatterplot, i.e., an MA plot, that shows the results from an experiment using the platform pipeline designed to identify any phenotypic variation for vector production within the library. FIG. 5B demonstrates a large dynamic range of a phenotype quantified by next generation sequencing. In this instance, a library of AAV capsid mutants reveals differential rates of assembly and genome packaging. Each point is a specific variant whose X coordinate is defined by the average abundance of the variant within the samples analyzed, and whose Y coordinate can be understood as the degree of enrichment of that variant within one or the other sample.

The results shown in FIG. 5B compare barcode counts from a vector preparation versus barcode counts from the plasmid library used to direct that vector preparation. Briefly, the count of a particular barcode was normalized to the total number of counts for that sequencing run, essentially turning the raw count into a percent proportion. This number was raised to the power of 1e6 to create a "counts per million" value. It is useful to covert this number into its log base 2 equivalent, allowing one to consider the counts in 2-fold increments. By subtracting the log 2 value for each barcode of one parameter (e.g., counts in the plasmid) from the other (e.g., counts in the vector), the resulting value can be interpreted as the 2-fold enrichment of any barcode in either parameter.

The MA plots if FIG. 5B are centered on the y-axis zero; points on this axis indicate no change in value between the parameters, whereas points above and below the axis indicate degree of enrichment as expressed in 2-fold increments. In this case, the difference between the maximum y-value and the minimum y-value represents a dynamic range of about 92-fold. The x-axis is simply the average count of each barcode between the parameters. This spreads the points out, and can be useful for further interpretation. This result indicates that the variability in this library contributes to a wide range of productivity/manufacturability phenotypes.

Example 3—Animal Experiments

Figure 6:
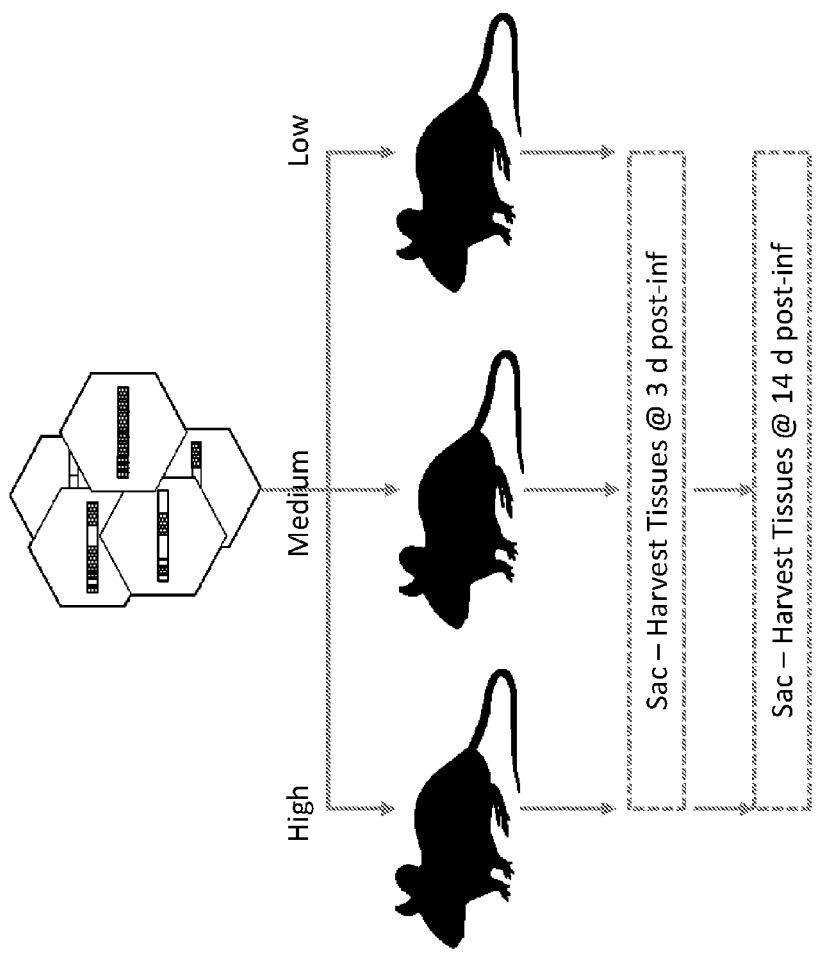
FIG. 6 is a flowchart showing an experimental protocol that employed the methods described herein in a mouse model.

FIG. 6 is a schematic of the animal experiments that were performed in the form of a flowchart showing the experimental protocol that employed the methods described herein in a mouse model. The goal of the animal experiments was to determine relative infectivity of members of an Anc80 combinatorial library over a range of three ten-fold doses, as determined by the number of times a barcode is counted in a tissue (see, for example, U.S. Pat. No. 9,695,220 for a description of Anc80) and to establish a minimum dose required to observe reproducibility in barcode counts between experimental subjects.

A combinatorial vector library produced using the methods described herein was used to infect mice at varying doses. Three animals per dose were used for a total of 15 mice. A high dose was administered at 2.69E11 gc; a medium dose was administered at 2.69E10 gc, and a low dose was administered at 2.69E9 cg. The route of administration was retro-orbital, allowing for systemic dissemination of the vector. Mice from each group were sacrificed at 3 days post-infection or 14 days post-infection and tissues were evaluated. DNA and/or RNA from the mice was obtained and analyzed by sequencing the barcode.

Figure 7C:
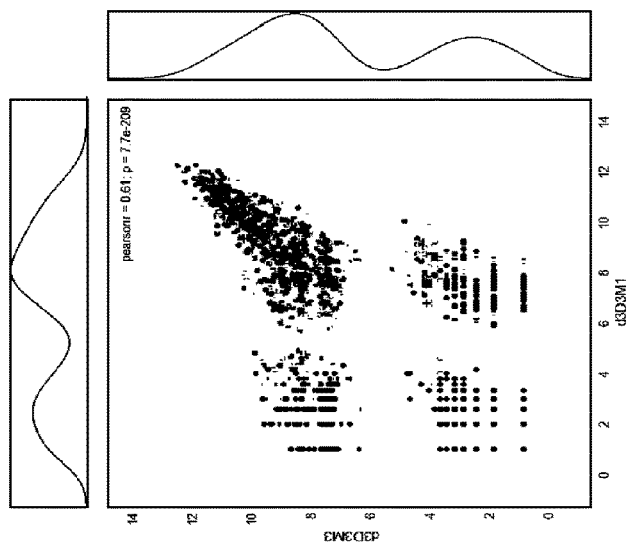
FIGS. 7A-7C are a series of scatterplots, similar to FIG. 5A, of data from the experiments illustrated in FIG. 6. These three plots demonstrate that barcode reproducibility in the liver varies with dose.
Figure 7B:
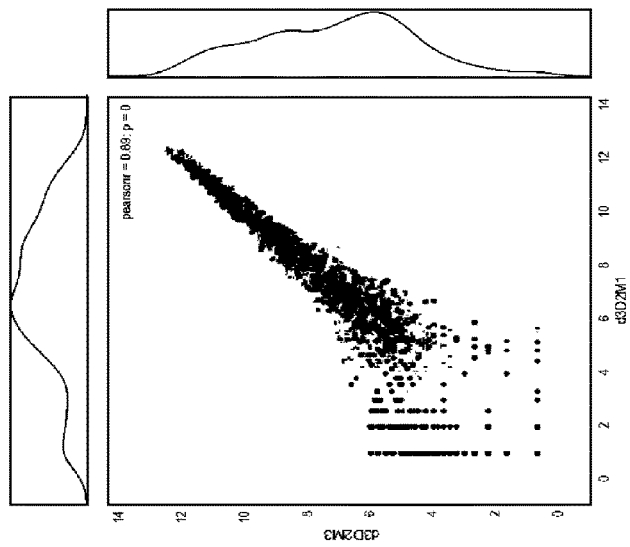
Figure 7A:
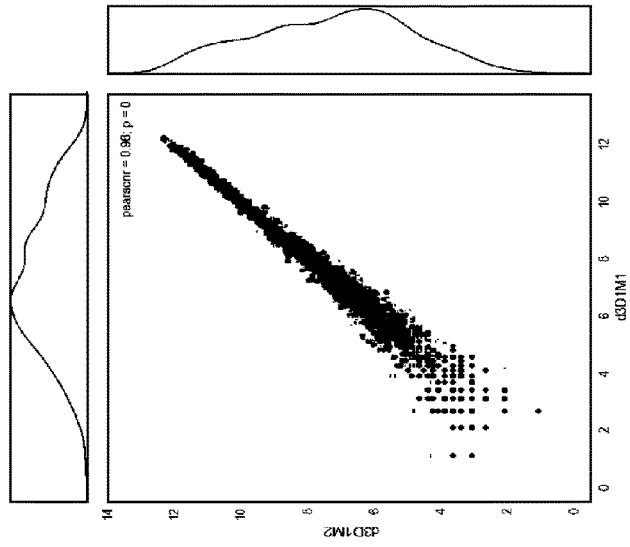

As shown in the scatterplots of FIGS. 7A and 7B, the results indicate that barcode counts recovered from two independent livers varied with dose. These plots demonstrate that barcode reproducibility in the liver varies with dose. FIG. 7A shows a scatterplot of barcodes recovered, sequenced, and counted from the livers of two animals infected with the highest does, 2.69E11 gc/mouse. At the highest dose, there was a range of infectivity observed, and this range of infectivity in the two livers was highly reproducible, with a high Pearson's correlation coefficient. FIG. 7B shows a scatterplot of barcodes recovered, sequenced, and counted from the livers of two animals infected with the middle dose, 2.69E10 gc/mouse. At the middle dose, a range of infectivity was still observed, but noise began to appear in the barcodes with lower overall counts (towards the origin) that affected the Pearson's value. FIG. 7C shows a scatterplot of barcodes recovered, sequenced, and counted from the livers of two animals infected with the lowest dose, 2.69E9 gc/mouse. The data is normalized, hence the identical axes, but the underlying absolute counts decrease with dose. At the lowest dose, some correlation of infectivity was observed for the most abundant barcodes, but the counts of the less-abundant barcodes were too low to assign an infectivity phenotype to those variants.

OTHER EMBODIMENTS

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of generating a combinatorial library, the method comprising:
   providing a first acceptor sequence comprising a first portion of an acceptor target sequence and a first portion of a corresponding acceptor barcode sequence;
   providing a first donor sequence comprising a first portion of a donor target sequence and a first portion of a corresponding donor barcode sequence;
   cleaving the first acceptor sequence between the first portion of the acceptor target sequence and the first portion of the corresponding acceptor barcode sequence; and
   ligating the first donor sequence into the cleaved first acceptor sequence,
   thereby producing a second acceptor sequence comprising a second portion of an acceptor target sequence and a second portion of a corresponding acceptor barcode sequence.

2. The method of claim 1, further comprising:
   providing a second donor sequence comprising a second portion of a donor target sequence and a second portion of a corresponding donor barcode sequence;
   cleaving the second acceptor sequence between the second portion of the acceptor target sequence and the second portion of the corresponding acceptor barcode sequence; and
   ligating the second donor sequence into the cleaved second acceptor sequence,
   thereby producing a third acceptor sequence comprising a third portion of an acceptor target sequence and a third portion of a corresponding acceptor barcode sequence.

3. The method of claim 2, further comprising repeating the providing, cleaving, and ligating steps a plurality of times with a third donor sequence and a fourth donor sequence to produce a third acceptor sequence and a fourth acceptor sequence, respectively, until the portions of acceptor target sequences generate a complete target sequence and the portions of corresponding acceptor barcode sequences generate a corresponding complete barcode sequence.

4. The method of claim 1, wherein each portion of the acceptor target sequence comprises at least one sequence variation and wherein each portion of the corresponding barcode sequence is unique to each of the at least one sequence variation.

5. The method of claim 3, wherein the complete target sequence is selected from the group consisting of a coding sequence, a promoter sequence, an untranslated region, and a polyadenylation signal.

6. The method of claim 5, wherein the untranslated region comprises an intron, an miRNA, or an RNA stability element.

7. The method of claim 5, wherein the coding sequence encodes a reporter gene, a viral capsid protein, a gene encoding a therapeutic protein, or a sequence that can be engineered.

8. The method of claim 3, wherein the complete barcode sequence is between about 80 bp and about 100 bp in length.

9. The method of claim 1, wherein the cleaving steps comprise the use of a Type II restriction endonuclease enzyme.

10. A method of screening a combinatorial library for a specific phenotype, the method comprising:
- introducing the combinatorial library produced by the method of claim 3 into a host cell under conditions in which the complete target sequence is functional;
- applying a selective condition on the host cells comprising the combinatorial library; and
- screening the host cells for the specific phenotype.

11. The method of claim 10, further comprising identifying a member of the combinatorial library in the host cells exhibiting the desired phenotype.

12. The method of claim 11, wherein the identifying step comprises high-throughput next generation sequencing.

13. The method of claim 10, wherein the host cells are cultured in vitro.

14. The method of claim 10, wherein the host cells are in a living animal.

15. The method of claim 14, wherein the host cells are in a specific tissue within the animal.

16. The method of claim 10, wherein the selective condition is selected from the group consisting of neutralizing antibody resistance, innate and adaptive immunity resistance, tissue tropism, gene transfer efficiency, gene expression efficiency, gene expression stability, serum stability, yield, affinity-column binding, charged resin binding, thermal stability, a range of pH tolerance, and repeat freeze-thaw tolerance.

17. A combinatorial library made by a method comprising the methods of claim 1.

18. The method of claim 7, wherein the sequence that can be engineered is selected from an antibody and a nuclease enzyme.

19. The method of claim 18, wherein the nuclease enzyme is selected from a Cas enzyme or a zinc-finger nuclease.

* * * * *